(12) United States Patent
Ascheman et al.

(10) Patent No.: US 8,241,911 B2
(45) Date of Patent: *Aug. 14, 2012

(54) CALIBRATION CARD FOR PHOTOLUMINESCENT OXYGEN SENSORS WITH ZERO POINT MAINTAINED WITH A METAL-AIR BATTERY

(75) Inventors: Timothy A. Ascheman, Elk River, MN (US); Daniel W. Mayer, Wyoming, MN (US); Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 29 days.

This patent is subject to a terminal disclaimer.

(21) Appl. No.: 12/950,018

(22) Filed: Nov. 19, 2010

(65) Prior Publication Data

US 2011/0154881 A1    Jun. 30, 2011

Related U.S. Application Data

(63) Continuation-in-part of application No. 12/633,110, filed as application No. PCT/US2009/063037 on Nov. 3, 2009, now Pat. No. 8,093,055.

(60) Provisional application No. 61/112,434, filed on Nov. 7, 2008.

(51) Int. Cl.
*G01D 18/00* (2006.01)
*G01N 21/76* (2006.01)
*G01N 1/22* (2006.01)

(52) U.S. Cl. ............... 436/9; 436/8; 436/127; 436/136; 436/164; 436/166; 436/167; 436/169; 436/172; 436/181; 422/420; 422/82.05; 422/82.08; 422/83; 422/88; 73/1.01; 73/1.02; 73/1.03; 73/1.06; 356/437; 356/440; 324/426; 136/290; 136/291

(58) Field of Classification Search .................. 436/8, 9, 436/127, 136, 138, 164, 166, 167, 169, 172, 436/174, 181; 422/400, 420, 82.05, 82.08, 422/83, 86, 88, 500, 547, 551; 73/1.01, 1.02, 73/1.03, 1.06; 356/436, 437, 440; 206/703; 324/426; 136/290, 291
See application file for complete search history.

(56) References Cited

U.S. PATENT DOCUMENTS 3,612,866 A    10/1971    Stevens
(Continued)

FOREIGN PATENT DOCUMENTS

WO    9004268 A1    4/1990
(Continued)

OTHER PUBLICATIONS

Lee, Sang-Kyung et al., "Photoluminescent Oxygen Sensing on a Specific Surface Area Using Phosphorescence Quenching of Pt-Pophyrin", Analitical Sciences, Departament of Bioengineering, Tokyo Institute of Technology, pp. 535-540, Aug. 1997, vol. 13.

(Continued)

*Primary Examiner* — Maureen Wallenhorst
(74) *Attorney, Agent, or Firm* — Sherrill Law Offices, PLLC

(57) ABSTRACT

A calibration card and method of using the card to calibrate an analytical instrument capable of reading a photoluminescent oxygen probe. The card includes at least (a) a first mass of an oxygen sensitive photoluminescent dye retained within a hermetically sealed space so as to isolate the dye from environmental oxygen, and in fluid communication with an activated metal-air battery whereby any oxygen permeating into the hermetically sealed space is quickly consumed by the battery, and (b) a second mass of an oxygen sensitive photoluminescent dye in fluid communication with the environment whereby the second mass of photoluminescent dye is exposed to an environmental concentration of oxygen.

38 Claims, 3 Drawing Sheets

U.S. PATENT DOCUMENTS

| | | | |
|---|---|---|---|
| 4,476,870 A | 10/1984 | Peterson et al. | |
| 4,810,655 A | 3/1989 | Khalil et al. | |
| 4,947,850 A | 8/1990 | Vanderkooi et al. | |
| 5,407,829 A | 4/1995 | Wolfbeis et al. | |
| 5,483,819 A | 1/1996 | Barmore et al. | |
| 5,695,640 A | 12/1997 | Tseng | |
| 5,718,842 A | 2/1998 | Papkovsky et al. | |
| 5,837,865 A | 11/1998 | Vinogradov et al. | |
| 5,902,467 A * | 5/1999 | Wang et al. | 204/415 |
| 6,060,196 A | 5/2000 | Gordon et al. | |
| 6,153,701 A | 11/2000 | Potnis et al. | |
| 6,165,741 A | 12/2000 | Wilson et al. | |
| 6,171,368 B1 * | 1/2001 | Maget et al. | 95/54 |
| 6,330,464 B1 | 12/2001 | Colvin et al. | |
| 6,362,175 B1 | 3/2002 | Vinogradov et al. | |
| 6,379,969 B1 | 4/2002 | Mauze et al. | |
| 6,395,555 B1 | 5/2002 | Wilson et al. | |
| 6,689,438 B2 | 2/2004 | Kennedy et al. | |
| 6,777,479 B1 | 8/2004 | Bernard et al. | |
| 7,135,342 B2 | 11/2006 | Colvin et al. | |
| 7,138,270 B2 | 11/2006 | Papkovsky et al. | |
| 7,368,153 B2 | 5/2008 | Barmore et al. | |
| 7,534,615 B2 | 5/2009 | Havens et al. | |
| 7,569,395 B2 | 8/2009 | Havens et al. | |
| 7,740,965 B2 | 6/2010 | Richards et al. | |
| 8,093,055 B2 * | 1/2012 | Mayer et al. | 436/9 |
| 2002/0164813 A1 | 11/2002 | Colvin, Jr. et al. | |
| 2003/0062262 A1 | 4/2003 | Mansouri et al. | |
| 2006/0002822 A1 | 1/2006 | Papkovsky et al. | |
| 2006/0144811 A1 * | 7/2006 | Cheng | 215/222 |
| 2007/0212789 A1 | 9/2007 | Havens et al. | |
| 2008/0051646 A1 | 2/2008 | Papkovsky et al. | |
| 2008/0117418 A1 | 5/2008 | Claps et al. | |
| 2008/0146460 A1 | 6/2008 | Pollok et al. | |
| 2008/0148817 A1 | 6/2008 | Miller et al. | |
| 2008/0190172 A1 | 8/2008 | Jones | |
| 2008/0199360 A1 | 8/2008 | Shahriari | |
| 2008/0215254 A1 | 9/2008 | Leiner et al. | |
| 2008/0242870 A1 | 10/2008 | Meador et al. | |
| 2009/0028756 A1 | 1/2009 | Shahriari | |
| 2009/0029402 A1 | 1/2009 | Papkovsky | |
| 2011/0136247 A1 * | 6/2011 | Papkovsky et al. | 436/136 |
| 2011/0154881 A1 | 6/2011 | Ascheman et al. | |
| 2011/0223678 A1 | 9/2011 | Ascheman et al. | |

FOREIGN PATENT DOCUMENTS

| | | |
|---|---|---|
| WO | 2007120637 A2 | 10/2007 |
| WO | 2010053888 A1 | 5/2010 |

OTHER PUBLICATIONS

Eaton, K. et al., "Effect of Humidity on the Response Characteristics of Luminescent PtOEP Thin Film Optical Oxygen Sensors", Sensors & Actuarors B, Elsevier Science B. V., vol. 82, pp. 94-104, 2002.

Technical Manual, "Freudenberg Grafted Products", Sep. 2006, pp. 1-32.

Papkovsky, D. et al., "Phosphorescent Sensor Aproach for Non-Destructive Measurments of Oxygen in Packaged Foods: Optimisation of Disposable Oxygen Sensors and Their Characterization Over a Wide Temperature Range", Departament of Biochemistry National University of Ireland, Analitical Letters, 33 (9), pp. 1755-1777, 2000.

* cited by examiner

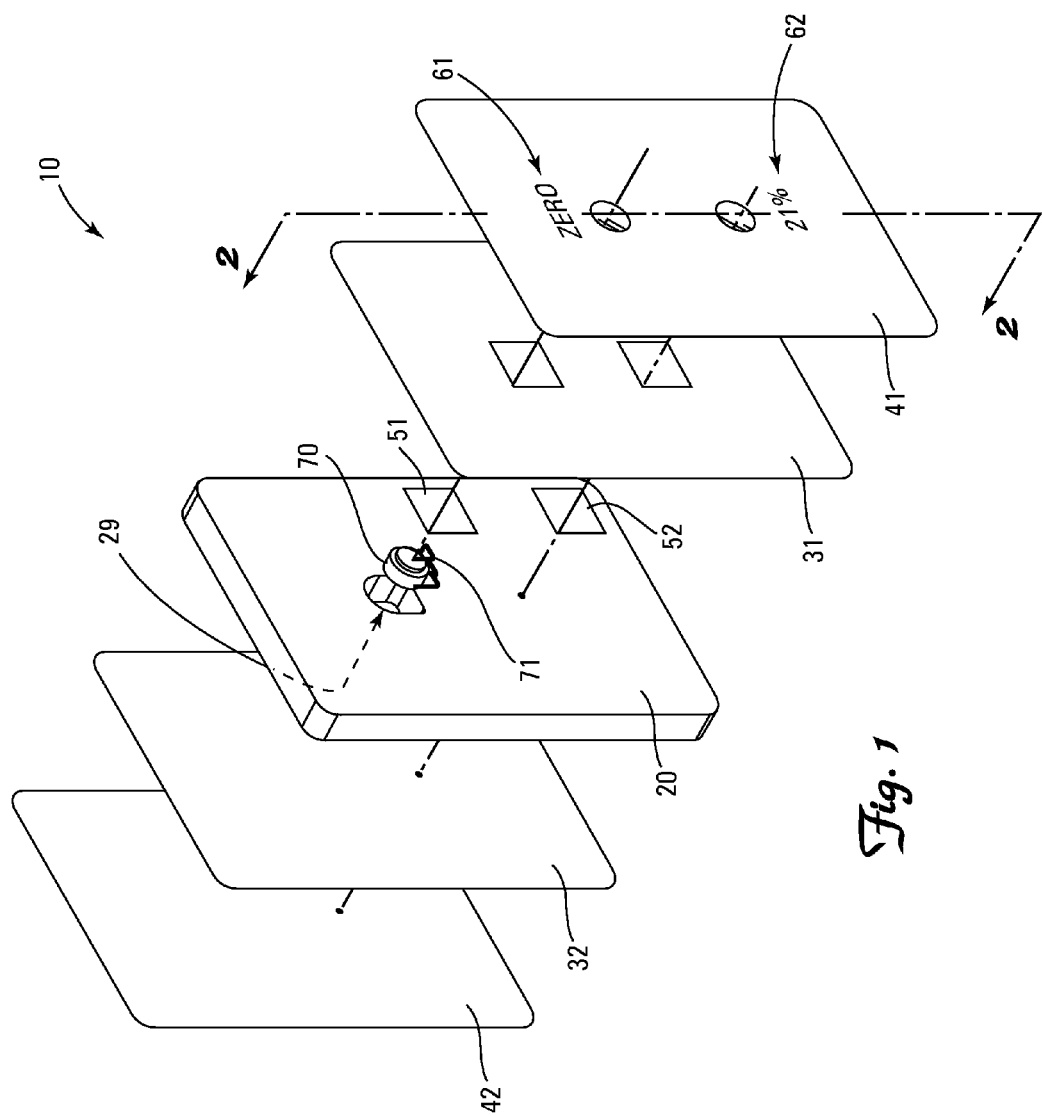

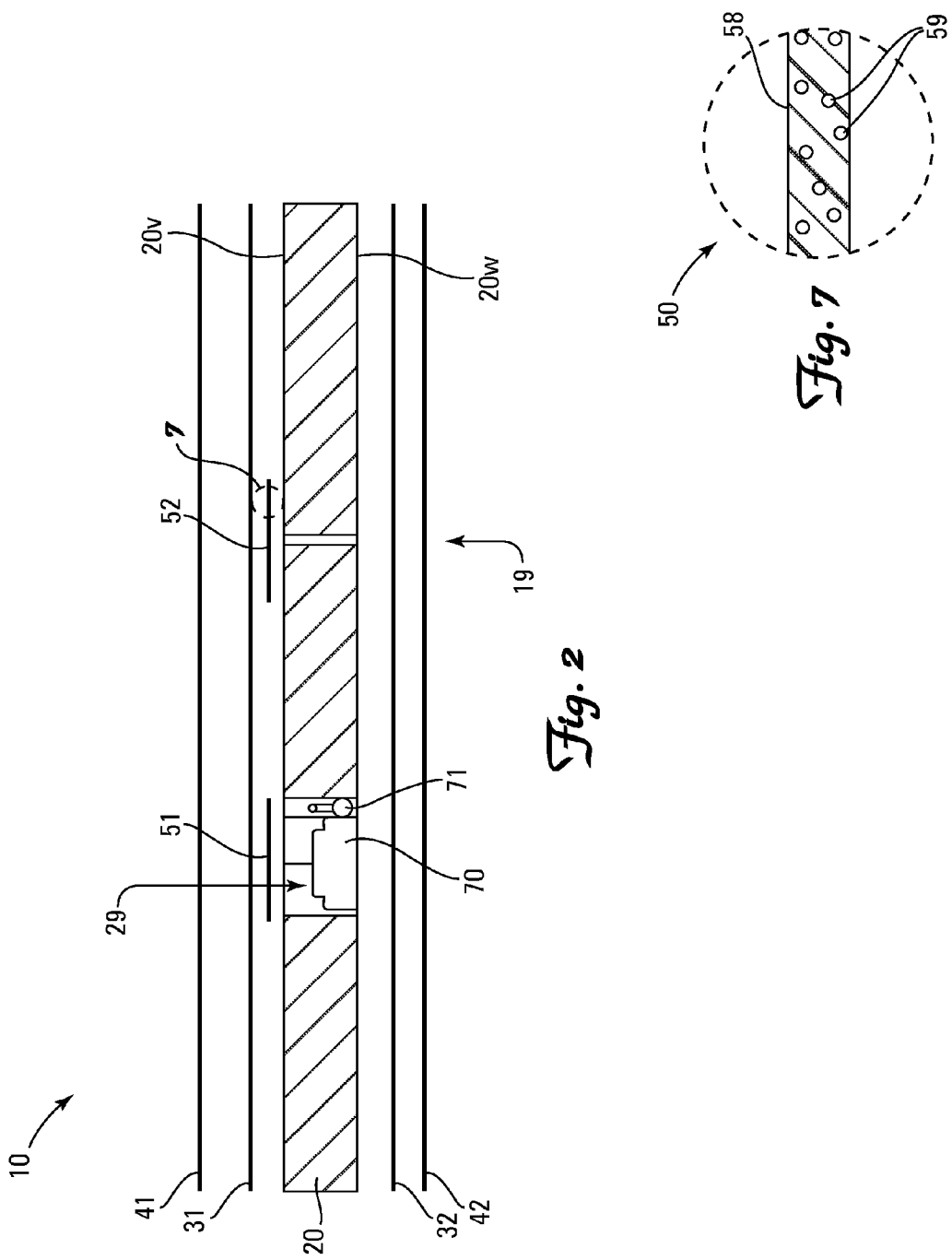

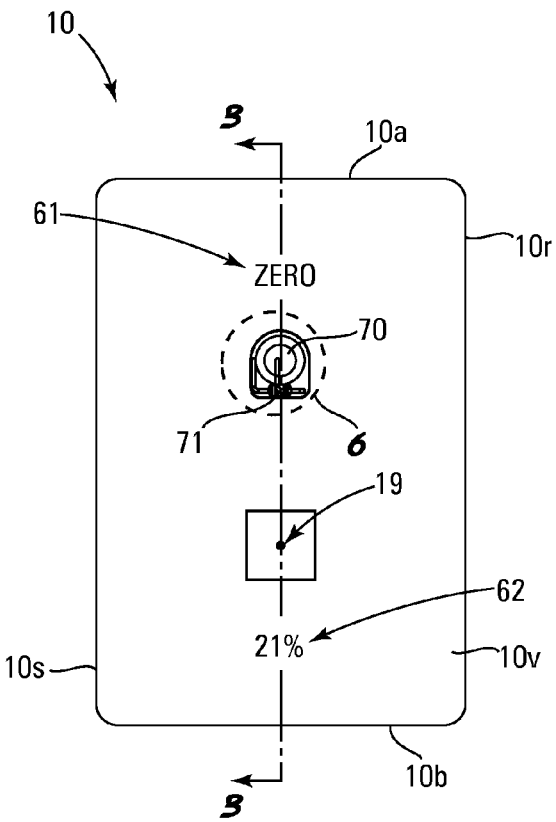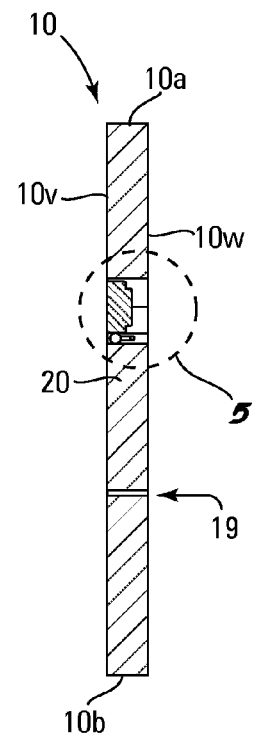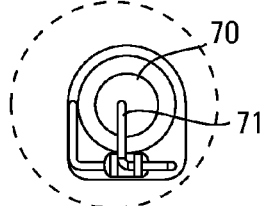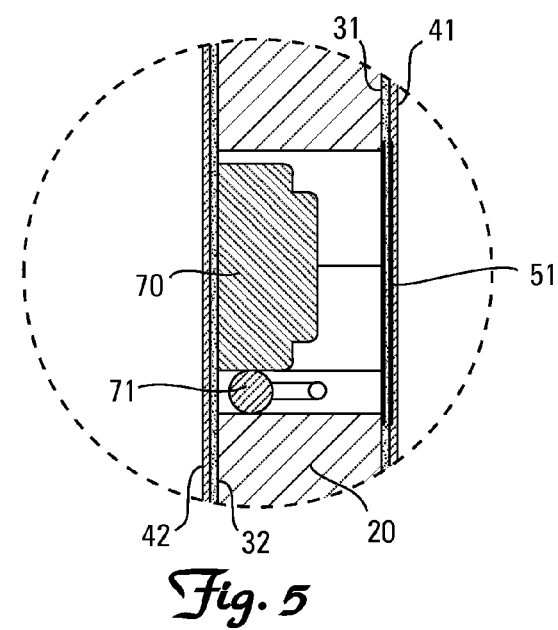

US 8,241,911 B2

CALIBRATION CARD FOR PHOTOLUMINESCENT OXYGEN SENSORS WITH ZERO POINT MAINTAINED WITH A METAL-AIR BATTERY

This application is a continuation-in-part of U.S. patent application Ser. No. 12/633,110 filed Dec. 8, 2009, now U.S. Pat. No. 8,093,055, issued on Jan. 10, 2012, which is a continuation-in-part of International Patent Application Serial No. PCT/US2009/063037 filed Nov. 3, 2009, which claims the benefit of U.S. Provisional Application No. 61/112,434 filed Nov. 7, 2008.

BACKGROUND

Photoluminescent sensors or probes are a widely employed method of measuring analyte concentration, typically oxygen, within an enclosed space such as a package or container. Briefly, analyte concentration within a package or container can be measured by placing an analyte sensitive photoluminescent probe within the package or container, allowing the probe to equilibrate within the package or container, exciting the probe with radiant energy, and measuring the extent to which radiant energy emitted by the excited probe is quenched by the presence of the target analyte. Such optical sensors are available from a number of suppliers, including Presens Precision Sensing, GmbH of Regensburg, Germany, Oxysense of Dallas, Tex., United States, and Luxcel Biosciences, Ltd of Cork, Ireland.

Analytical instruments used to read such photoluminescent probes are commonly programmed with a calibration mode that permits calibration of the instrument by having the instrument read probes that have been exposed to mediums having known concentrations of the target analyte (e.g., setting the instrument to calibration mode, reading a probe that has been placed within a container that is flushed with certified tank gas containing 0% analyte, and then reading a probe that has been placed within a container that is flushed with certified tank gas containing a known concentration(s) of analyte such as 100% analyte).

While effective for accurately calibrating optical sensors, this calibration method is time consuming and expensive.

Accordingly, a substantial need exists for a low cost system and method for accurately and reliably calibrating instruments used to read photoluminescent sensors or probes.

SUMMARY OF THE INVENTION

A first aspect of the invention is a calibration card for use in calibrating an analytical instrument capable of reading an oxygen sensitive photoluminescent probe from which the concentration of oxygen in a sample communicating with the probe can be determined.

A first embodiment of the first aspect of the invention is a calibration card that includes at least (a) a first mass of an oxygen sensitive photoluminescent dye retained within a hermetically sealed space so as to isolate the dye from environmental oxygen, and in fluid communication with an activated metal-air battery whereby any oxygen in the hermetically sealed space is consumed by the battery, and (b) a second mass of an oxygen sensitive photoluminescent dye in fluid communication with the environment whereby the second mass of photoluminescent dye is exposed to an environmental concentration of oxygen.

A second embodiment of the first aspect of the invention is a calibration card that includes at least (a) a first probe isolated from environmental oxygen and in fluid communication with an activated metal-air battery effective for scavenging oxygen from the first probe, whereby the concentration of oxygen in communication with the first probe can be reduced and maintained near zero, and (b) a second probe in fluid communication with the environment for allowing the second probe to communicate with an environmental concentration of oxygen.

A second aspect of the invention is a method of calibrating an optical oxygen sensor having a calibration mode that is capable of reading an oxygen sensitive photoluminescent probe from which the concentration of oxygen in a sample communicating with the probe can be determined.

A first embodiment of the second aspect includes the steps of (a) obtaining a calibration card according to the first embodiment of the first aspect of the invention, (b) setting the optical oxygen sensor to calibration mode, and (c) sequentially taking an oxygen concentration reading from each of the masses of oxygen sensitive photoluminescent dye such that the oxygen concentration reading is correlated with the known oxygen concentration to which the mass of oxygen sensitive photoluminescent dye is exposed.

A second embodiment of the second aspect includes the steps of (a) obtaining a calibration card according to the second embodiment of the first aspect of the invention, (b) exposing the second probe on the calibration card to a medium having a known concentration of oxygen, (c) setting the analytical instrument to calibration mode, (d) taking a reading from the first probe with the analytical instrument, (e) correlating the value of the reading to a zero oxygen concentration, (f) taking a reading from the second probe with the analytical instrument, and (g) correlating the value of the reading to the known oxygen concentration to which the second probe is exposed.

BRIEF DESCRIPTION OF THE DRAWINGS

FIG. 1 is an exploded perspective view of one embodiment of the invention.

FIG. 2 is an exploded cross-sectional side view of the invention depicted in FIG. 1 taken along line 2-2.

FIG. 3 is a top assembled view of the invention depicted in FIG. 1.

FIG. 4 is a cross-sectional side view of the invention depicted in FIG. 3 taken along line 3-3.

FIG. 5 is an enlarged cross-sectional detailed side view of a portion of the invention depicted in FIG. 4 encompassing the second or 0% mass of photoluminescent composition and associated battery.

FIG. 6 is an enlarged top view of a portion of the invention depicted in FIG. 4 encompassing the second or 0% mass of photoluminescent composition and associated battery.

FIG. 7 is a microscopically enlarged cross-sectional side view of one embodiment of a photoluminescent composition suitable for use as the first and second masses of photoluminescent composition in the present invention.

DETAILED DESCRIPTION OF A PREFERRED EMBODIMENT

Definitions

As used herein, including the claims, the phrase "metal-air battery" means an electrochemical battery or fuel cell powered by oxidizing a metal, such as cadmium, lead, lithium or zinc, with ambient oxygen, typically air.

As used herein, including the claims, the phrase "activated metal-air battery" means a metal-air battery with air access hole(s) to the cathode are open to the environment (i.e., the oxygen barrier film typically placed over the air access hole(s) has been removed to permit air to enter the cell).

As used herein, including the claims, the phrase "near zero", when used to describe a concentration of oxygen in a sample, means less than 0.01% oxygen.

As used herein, including the claims, the phrase "oxygen impermeable" means a material that when formed into a 1 mil (25.4 µm) film has an oxygen transmission rate of less than 100 $c^3/m^2$ day when measured in accordance with ASTM F 1927.

As used herein, including the claims, the phrase "oxygen barrier" means a film, including coated, metalized and multiple layer films, that are impervious to oxygen (such as a layer of metal) or have an oxygen transmission rate of less than 20 $c^3/m^2$ day when measured in accordance with ASTM F 1927.

As used herein, including the claims, the phrase "oxygen sensitivity" or "sensitivity to oxygen" means sensitivity measured by luminescence quenching.

As used herein, including the claims, the phrase "thin film" means a film having a thickness of less than 10 µm.

NOMENCLATURE

10 Calibration Card
10a Top of Calibration Card
10b Bottom of Calibration Card
10r Right Side of Calibration Card
10s Left Side of Calibration Card
10v Upper Major Surface of Calibration Card
10w Lower Major Surface of Calibration Card
19 Exposure Channel through Spacer and Lower Layers
20 Intermediate Spacer Layer
20v Upper Major Surface of Spacer Layer
20w Lower Major Surface of Spacer Layer
29 Retention Well in Spacer Layer
31 Upper Adhesive Layer
32 Lower Adhesive Layer
41 Upper Cover Layer
42 Lower Base Layer
50 Masses Photoluminescent Compositions
51 First or 0% Mass of Solid State Photoluminescent Composition
52 Second or 21% Mass of Solid State Photoluminescent Composition
58 Carrier Matrix
59 Oxygen-Sensitive Photoluminescent Dye
60 Indicia
61 First Indicia Indicating First or 21% Mass of Solid State Photoluminescent Composition
62 Second Indicia Indicating Second or 0% Mass of Solid State Photoluminescent Composition
70 Battery
71 Load Powered by Battery Construction Referring generally to FIGS. 1-4, a first aspect of the invention is a calibration card 10 for use in calibrating an analytical instrument (not shown) for reading photoluminescent sensors or probes (not shown). The calibration card 10 includes first 51 and second 52 masses of an oxygen sensitive photoluminescent composition 50. The first mass of oxygen sensitive photoluminescent composition 51 is isolated from the surrounding environment and in fluid communication with an oxygen consuming zinc-air battery 70 for scavenging oxygen from the hermetically sealed first mass 51. The second mass of oxygen sensitive photoluminescent composition 52 is in fluid communication with the surrounding environment for exposing the second mass 52 to an environmental concentration of oxygen.

Referring to FIG. 7, the first mass 51 (also referenced as the 0% mass for convenience) and the second mass 52 (also referenced as the 21% mass for convenience) each comprise an oxygen-sensitive photoluminescent dye 59 that is the same as the oxygen-sensitive photoluminescent dye employed in the probes (not shown) read by the instrument (not shown), embedded within an oxygen permeable carrier matrix 58 that is the same as the carrier matrix employed in the probes (not shown) read by the instrument (not shown).

FIGS. 1 and 2 depict the constructional components of one embodiment of a calibration card 10 in accordance with this invention. The calibration card 10 depicted in FIGS. 1 and 2, includes laterally spaced first and second masses of oxygen sensitive photoluminescent composition 51 and 52 (collectively referenced as photoluminescent masses 50) mounted onto a first major surface 20v of an intermediate spacer layer 20 and sandwiched between an upper cover layer 41 and a lower base layer 42. The spacer layer 20, upper cover layer 41, and lower base layer 42 are all effective as an oxygen barrier. The first mass of oxygen sensitive photoluminescent composition 51 is in fluid communication with an activated metal-air battery 70 retained within a retention well 29 within the spacer layer 20. The second mass of oxygen sensitive photoluminescent composition 52 is placed in fluid communication with the surrounding environment via a channel 19 through the spacer layer 20 and lower base layer 42. Adhesive layers 31 and 32 secure the upper cover layer 41 and lower base layer 42 to the upper major surface 20v and lower major surface 20w of the spacer layer 20, respectively, thereby sandwiching the first and second photoluminescent masses 50 between the oxygen barrier upper cover layer 41 and lower base layer 42.

The calibration card 10 has a top edge 10a, a bottom edge 10b, a right side edge 10r, a left side edge 10s, an upper major surface 10v and a lower major surface 10w. The card 10 should have a length of about 4 to 20 cm, a width of about 4 to 20 cm, and a thickness of less than 1 cm. A card 10 smaller than this is prone to being lost or misplaced while a card 10 larger than this becomes unnecessarily bulky. The card 10 preferably has a length of about 6 to 10 cm, a width of about 4 to 8 cm, and a thickness of about 0.5 to 1 cm, and most preferably approximates the length and width of a standard credit card (i.e., about 8.5 cm long and 5.5 cm wide).

The card 10 should be durable and wear resistant.

The intermediate spacer layer 20 contributes the bulk of the structural integrity to the card 10 and provides the thickness necessary to accommodate the metal-air battery 70. The spacer layer 20 may be transparent, translucent or opaque as desired. The spacer layer 20 should be relatively impermeable to $O_2$ for purposes of limiting the rate at which $O_2$ can permeate through the edges (10a, 10b, 10r and 10s) of the card 10 and into contact with the first mass of oxygen sensitive photoluminescent composition 51. Suitable materials include specifically, but not exclusively, plastics such as an acrylic or polyethylene terephthalate; and metals such as aluminum, copper or steel.

The cover layer 41 provides some additional structural integrity to the card 10 and serves as a protective covering for the photoluminescent masses 50. The cover layer 41 needs to be transparent or translucent at least at the specific wavelengths at which the photoluminescent masses 50 absorb and emit energy. The cover layer 41 serves as an oxygen barrier for reducing the rate at which oxygen permeates through the card 10 and into contact with the first mass of oxygen sensitive photoluminescent composition 51. Suitable materials include specifically, but not exclusively, plastics. Preferred plastics are mylar and polyethylene terephthalate.

The base layer 42 also provides some additional structural integrity to the card 10. The base layer 42 need not be transparent or translucent as the photoluminescent masses 50 are not interrogated through the base layer 42. The base layer 42, as with the cover layer 41, serves as an oxygen barrier for reducing the rate at which oxygen permeates through the card 10 and into contact with the first mass of oxygen sensitive photoluminescent composition 51. Suitable materials include specifically, but not exclusively, plastics. Preferred plastics are mylar and polyethylene terephthalate.

Adhesive layers 31 and 32 may be selected from a wide variety of adhesives suitable for use in laminating metal and plastic layers together, including various hot melt and pressure-sensitive adhesives. It may also be possible to forgo the use of the adhesive layer when the cover layer 41 and base layer 42 are capable of being bound directly to the intermediate spacer layer 20 such as by heat welding.

Referring to FIG. 7, the oxygen sensitive photoluminescent masses 50 include an oxygen-sensitive photoluminescent dye 59 embedded within an oxygen-permeable carrier matrix 58.

The same oxygen sensitive photoluminescent masses 50 are used for both the 0% and the 21% masses 51 and 52, and need to match the photoluminescent masses 50 used in the sensors or probes (not shown) that are read by the analytical instrument (not shown) being calibrated. Most preferably, the oxygen sensitive photoluminescent masses 50 and the probes (not shown) that are intended to be read by the instrument (not shown) are produced in the same run from the same batch of photoluminescent composition.

The oxygen-sensitive photoluminescent dye 59 may be selected from any of the well-known oxygen sensitive photoluminescent dyes used in the construction of oxygen sensitive photoluminescent probes (not shown). A nonexhaustive list of such oxygen sensitive photoluminescent dyes 59 includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium(III) or osmium(II).

The oxygen-sensitive photoluminescent dye 59 is compounded with a suitable carrier matrix 58. Compositions used as the carrier matrix 58 are oxygen-permeable compositions, preferably highly oxygen permeable compositions. One of routine skill in the art is capable of selecting such oxygen-permeable carrier compositions 58. A nonexhaustive list of polymers suitable for use as the carrier matrix 58 includes specifically, but not exclusively, silicone, polystyrene, polycarbonate, polysulfone, and some other polymers and co-polymers.

Typically, the oxygen sensitive photoluminescent masses 50 are coated onto a support layer (not shown). The support layer is typically a sheet or film formed from a material that is compatible with the oxygen sensitive photoluminescent masses 50. One of routine skill in the art is capable of selecting suitable support layer.

An activated metal-air battery 70 is retained within a retention well 29 in the intermediate spacer layer 20 and in fluid communication with the 0% oxygen sensitive photoluminescent mass 51 for consuming oxygen from around the hermetically sealed 0% oxygen sensitive photoluminescent mass 51.

Metal-air batteries, such as a zinc-air battery, are different from most other batteries in that they "breath" oxygen from the air for use as the cathode reactant. The electrochemical system can be more formally defined as zinc/potassium hydroxide/oxygen, but "zinc-air" is the widely used common name. Metal-air batteries are commercially available from a variety of sources, including The Gillette Company under the brand name Duracell®. A typical zinc-air cell consists of a zinc anode, an aqueous alkaline electrolyte and an air cathode. Power is derived from the reduction of oxygen at the cathode, and the oxidation of zinc at the anode. The simplified net reaction is shown below:

$$2Zn+O_2 \Rightarrow 2ZnO$$

The anode in a zinc air cell is typically powdered zinc amalgam. The zinc powder typically contains a very low level of mercury to prevent internal pressure buildup due to hydrogen evolution from the self-discharge of the zinc in the electrolyte. A gelling agent is also usually mixed with the zinc amalgam to maintain the uniformity of the zinc powder-electrolyte mixture during discharge.

In the cell reaction, the zinc in the anode is oxidized to form zinc hydroxide in the form of the soluble zincate $[Zn(OH)_4^{2-}]$ ion. The half reaction for the anode is shown below:

$$Zn+4OH^- \Rightarrow Zn(OH)_4^{2-}+2e^-$$

The zinc hydroxide accumulates around the zinc particle, but does not impede either ionic or particle-to-particle conductance until the zinc is fully oxidized. As the discharge proceeds, the zincate ions eventually precipitate to form zinc oxide (ZnO).

$$Zn(OH)_4^{2-} \Rightarrow ZnO+H_2O+2OH^-$$

The air cathode in a zinc-air cell is typically a mixture of carbon, Teflon, and a small amount of manganese dioxide impressed onto a nickel-plated screen. This material is then laminated with a Teflon layer on one side and a separating membrane on the other. The Teflon layer allows gases, most importantly oxygen, to diffuse into and out of the cell, and also provides resistance to leakage. The separator acts as an ion conductor between the electrodes and as an insulator to prevent internal short-circuiting.

Atmospheric oxygen reacts with catalysts in the air electrode and electrolyte to produce hydroxide ions. The half reaction for the air cathode is shown below:

$$O_2+2H_2O+4e^- \Rightarrow 4OH^-$$

The alkaline electrolyte typically employed in a zinc air cell is an aqueous solution of potassium hydroxide with a small amount of zinc oxide to prevent self-discharge of the anode. Potassium hydroxide provides good ionic conductance between the anode and cathode to permit efficient discharge of the cell.

The anode subassembly includes the anode can and the insulator. An exemplary anode can, which holds the zinc anode, is a tri-clad material comprised of a copper interior lining for good chemical compatibility, a stainless steel layer in the middle for strength, and nickel layer on the outside for good electrical contact. A nylon insulator surrounds this can and insulates the negative terminal from the positive terminal. A sealant coating is typically applied to the insulator prior to its assembly with the anode can. The cathode subassembly consists of the cathode can and the air electrode. An exemplary cathode can is made of nickel plated steel, and contains multiple air holes punched into the bottom to provide air access to the cathode. These air holes provide the pathway for oxygen to enter the cell.

A porous membrane is typically placed directly over the holes to facilitate uniform air distribution across the air electrode. A loose layer of Teflon is typically provided on top of this membrane to help form the cathode seal. The air electrode itself (i.e. cathode) is oriented with its Teflon side toward the air holes. There is an interference between the ends of the nickel screen that protrude from the perimeter of the cathode, and the cathode can to form a low resistance contact. The zinc-anode mix and the electrolyte are dispensed into the anode subassembly, over which the cathode subassembly is placed and sealed.

Once constructed, a tab that is placed over the air holes and attached via a mild adhesive to seal the cell and prevent environmental oxygen from entering the cell and contacting the cathode. The cell is activated by simply peeling off the tab.

The activated battery 70 must have an oxygen consumption rate that exceeds the permeation rate of oxygen into the sealed space containing the first mass of photoluminescent composition 51 from the surrounding air. An activated battery 70 that consumes oxygen at a rate that is less than the permeation rate of oxygen into the sealed space containing the first mass of photoluminescent composition 51 will result in an inaccurate calibration as the first mass of photoluminescent composition 51 will be exposed to an oxygen concentration well in excess of 0%. At the other extreme, an activated battery 70 that consumes oxygen at a rate that is significantly greater than the permeation rate of oxygen into the sealed space containing the first mass of photoluminescent composition 51 will cause the card 10 to structurally deform due to an internal pressure buildup caused by hydrogen evolution from a continuous and prolonged operation in an oxygen starved environment. Hence, the activated battery 70 preferably consumes oxygen at a rate that is only slightly greater than the permeation rate of oxygen into the sealed space containing the first mass of photoluminescent composition 51, with a generally acceptable range of between two to ten times the permeation rate of oxygen into the sealed space. With selection of good oxygen barrier materials for use as the intermediate spacer layer 20, the cover layer 41 and the base layer 42, the oxygen consumption rate achieved by an activated battery resulting from self-discharge is sufficient. However, should a higher rate of oxygen consumption be necessary or desired, a suitable load 71 may be operably connected to the battery 70. Typically, a load 71 having a resistance of at least 100,000Ω, preferably at least 500,000Ω, and most preferably at least 1,000,000Ω will provide the necessary and desired rate of oxygen consumption.

The upper major surface 10v of the card 10 is imprinted with first indicia 61 and second indicia 62 (collectively indicia 60) for identifying the first photoluminescent mass 51 as the mass representative of a probe (not shown) exposed to limited oxygen (e.g., 0%, Zero, Low, Minimum, etc.), and identifying the second photoluminescent mass 52 as the mass representative of a probe (not shown) exposed to an environmental concentration of oxygen (e.g., 21%, Twenty One, High, Maximum, Atmosphere, etc.).

The lifespan of the calibration card 10 is dictated by the effective life of the metal-air battery 70 employed in the card 10, which will typically be between one and three years from activation of the battery 70.

Use

The calibration card 10 can be used to quickly and easily calibrate an optical oxygen sensor (not shown) having a calibration mode. With the calibration card 10, calibration of an optical oxygen sensor (not shown) simply involves the steps of (1) setting the optical sensor to calibration mode, and (2) sequentially taking an oxygen concentration reading from each of the masses of oxygen sensitive photoluminescent composition 51 and 52 such that the oxygen concentration reading is correlated with the known oxygen concentration to which the mass of oxygen sensitive photoluminescent composition 51 and 52 is exposed.

Correlation of the oxygen concentration reading to the oxygen sensitive photoluminescent composition 51 or 52 from which the reading was taken can be accomplished in various ways. One technique is to take the oxygen concentration readings in a predetermined sequence previously input into the optical oxygen sensor (not shown). A second technique is to automatically provide the optical oxygen sensor (not shown) with additional data each time a reading is taken effective for indicating which of the masses of oxygen sensitive photoluminescent composition 51 and 52 was sensed (e.g., a unique bar code provided next to each mass 50 that is read each time a mass 50 is read). Yet a third technique is to provide the optical oxygen sensor (not shown) with additional data each time a reading is taken effective for indicating the oxygen concentration to which the sensed mass of oxygen sensitive photoluminescent composition 51 and 52 was exposed at the time of the reading (e.g., user input of 0 after the 0% mass 51 is read and user input of 21 after the 21% mass 52 is read).

Preferably, both the oxygen probes (not shown) and the calibration card 10 operate in photoluminescence lifetime mode. Luminescence lifetime measurements can be performed by any of the known methods, including specifically but not exclusively direct measurement of luminescence decay, measurement of luminescence phase shift, anisotropy, or any other parameter which is related directly or indirectly to the luminescence lifetime of the probe and the first and second masses 51 and 52.

We claim:

1. A calibration card for use in calibrating an optical oxygen sensor, comprising (i) a first mass of an oxygen sensitive photoluminescent dye retained within a hermetically sealed space so as to isolate the dye from environmental oxygen and thereby define a permeation rate of oxygen from the surrounding air into the sealed space, and in fluid communication with an activated metal-air battery whereby any oxygen in the hermetically sealed space is consumed by the battery, and (ii) a second mass of an oxygen sensitive photoluminescent dye in fluid communication with the environment whereby the second mass of photoluminescent dye is exposed to an environmental concentration of oxygen.

2. The calibration card of claim 1, wherein the card has a length of about 4 to 20 cm, a width of about 4 to 20 cm, and a thickness of less than 1 cm.

3. The calibration card of claim 2, wherein the first mass of oxygen sensitive photoluminescent dye is isolated from environmental oxygen by sandwiching the first mass of oxygen sensitive photoluminescent dye between an oxygen barrier support layer and an oxygen barrier cover layer.

4. The calibration card of claim 3, wherein the cover layer is a transparent layer of polyethylene terephthalate.

5. The calibration card of claim 3, wherein the first and second masses of oxygen sensitive photoluminescent dye are sandwiched between the oxygen barrier support layer and the oxygen barrier cover layer, with the second mass of oxygen sensitive photoluminescent dye in fluid communication with the environment via at least one hole through at least one of the support layer and the cover layer.

6. The calibration card of claim 1, wherein the oxygen sensitive photoluminescent dye in both the first and second masses are the same.

7. The calibration card of claim 1, wherein the activated battery has an oxygen consumption rate resulting from self-discharge that exceeds the permeation rate of oxygen into the sealed space containing the first mass of photoluminescent dye from the surrounding air.

8. The calibration card of claim 1, wherein the battery continuously powers a load having a resistance of at least 500,000 ohms, whereby the battery is effective for continuously consuming oxygen from the hermetically sealed space containing the first mass of photoluminescent dye.

9. The calibration card of claim 1, wherein the battery continuously powers a load having a resistance of at least 1,000,000 ohms, whereby the battery is effective for continuously scavenging oxygen from the hermetically sealed space containing the first mass of photoluminescent dye.

10. The calibration card of claim 1, wherein the battery continuously powers a load having a resistance selected to limit a rate of oxygen consumable by the battery as between (1) the permeation rate of oxygen into the sealed space containing the first mass of photoluminescent dye from the surrounding air, and (2) ten times this rate.

11. The calibration card of claim 1, wherein the battery continuously powers a load having a resistance selected to limit a rate of oxygen consumable by the battery as between (1) the permeation rate of oxygen into the sealed space containing the first mass of photoluminescent dye from the surrounding air, and (2) twice this rate.

12. The calibration card of claim 1 wherein the metal-air battery is a zinc-air button battery.

13. The calibration card of claim 1, wherein the card contains first indicia tagging the first mass of oxygen sensitive photoluminescent dye as an oxygen sensitive photoluminescent dye exposed to limited oxygen, and second indicia tagging the second mass of oxygen sensitive photoluminescent dye as oxygen sensitive photoluminescent dye exposed to an environmental concentration of oxygen.

14. The calibration card of claim 13, wherein the first indicia comprises at least the designation "0%" or "zero", and the second indicia comprises at least the designation "21%" or "air".

15. A method of calibrating an optical oxygen sensor having a calibration mode, comprising the steps of:
   (a) obtaining a calibration card according to claim 1 with the first mass of oxygen sensitive photoluminescent dye exposed to a known near-zero concentration of oxygen and the second mass of oxygen sensitive photoluminescent dye exposed to a known environmental concentration of oxygen,
   (b) setting the optical oxygen sensor to calibration mode, and
   (c) sequentially taking an oxygen concentration reading from each of the masses of oxygen sensitive photoluminescent dye such that the oxygen concentration reading is correlated with the known oxygen concentration to which the mass of oxygen sensitive photoluminescent dye is exposed.

16. The method of claim 15, wherein step (c) comprises at least the step of taking an oxygen concentration reading from each of the masses of oxygen sensitive photoluminescent dye in a predetermined sequence.

17. The method of claim 15, wherein step (c) comprises at least the steps of: (1) sensing the oxygen concentration to which one of the masses of oxygen sensitive photoluminescent dye is exposed using the optical sensor in calibration mode, (2) providing the optical sensor with data indicating which of the masses of oxygen sensitive photoluminescent dye on the calibration card was sensed, and (3) sensing the oxygen concentration to which the other mass of oxygen sensitive photoluminescent dye is exposed using the optical sensor in calibration mode.

18. The method of claim 15, wherein step (c) comprises at least the steps of: (1) sensing the oxygen concentration to which one of the masses of oxygen sensitive photoluminescent dye is exposed using the optical sensor in calibration mode, (2) providing the optical sensor with data indicating the known oxygen concentration to which the one mass of oxygen sensitive photoluminescent dye is exposed, (3) sensing the oxygen concentration to which the other mass of oxygen sensitive photoluminescent dye is exposed using the optical sensor in calibration mode, and (4) providing the optical sensor with data indicating the known oxygen concentration to which the other mass of oxygen sensitive photoluminescent dye is exposed.

19. The method of claim 15, wherein the first mass of oxygen sensitive photoluminescent dye is sandwiched between an oxygen barrier support layer and an oxygen barrier transparent cover layer.

20. The method of claim 15, wherein the activated battery has an oxygen consumption rate resulting from self-discharge that exceeds the permeation rate of oxygen into the sealed space containing the first mass of photoluminescent dye from the surrounding air.

21. The method of claim 15, wherein the battery continuously powers a load having a resistance of at least 100,000 ohms, whereby the battery is effective for continuously consuming oxygen from the hermetically sealed space containing the first mass of photoluminescent dye.

22. The method of claim 15, wherein the battery continuously powers a load having a resistance of at least 500,000 ohms, whereby the battery is effective for continuously scavenging oxygen from the hermetically sealed space containing the first mass of photoluminescent dye.

23. The method of claim 15, wherein the battery continuously powers a load having a resistance selected to limit a rate of oxygen consumable by the battery as between (1) the permeation rate of oxygen into the sealed space containing the first mass of photoluminescent dye from the surrounding air, and (2) ten times this rate.

24. The method of claim 15, wherein the battery continuously powers a load having a resistance selected to limit a rate of oxygen consumable by the battery as between (1) the permeation rate of oxygen into the sealed space containing the first mass of photoluminescent dye from the surrounding air, and (2) twice this rate.

25. The method of claim 15, wherein the calibration card contains first indicia tagging the first mass of oxygen sensitive photoluminescent dye as an oxygen sensitive photoluminescent dye exposed to limited oxygen, and second indicia tagging the second mass of oxygen sensitive photoluminescent dye as oxygen sensitive photoluminescent dye exposed to an environmental concentration of oxygen.

26. A calibration card for use in calibrating an analytical instrument capable of reading a photoluminescent oxygen probe from which the concentration of oxygen in a sample communicating with the probe can be determined, wherein the probe comprises an oxygen-sensitive photoluminescent dye embedded within an oxygen-permeable carrier matrix, the calibration card comprising:
   (a) a first probe isolated from environmental oxygen and in fluid communication with an activated metal-air battery effective for scavenging oxygen from the first probe, whereby the concentration of oxygen in communication with the first probe can be reduced and maintained near zero, and (b) a second probe in fluid communication with the environment for allowing the second probe to communicate with an environmental concentration of oxygen.

27. The calibration card of claim 26 wherein the oxygen-sensitive photoluminescent dye is a transition metal complex selected from the group consisting of a ruthenium bipyridyl, a ruthenium diphenylphenanotroline, a platinum porphyrin, a palladium porphyrin, a phosphorescent complex of a tetrabenzoporphyrin, a chlorin, a porphyrin-ketone, an aza-porphyrin and a long-decay luminescent complex of iridium(III) or osmium(III).

28. The calibration card of claim 26 wherein the oxygen-permeable carrier matrix is selected from the group consisting of silicone, polystryrene, polycarbonate, and polysulfone.

29. The calibration card of claim 26 wherein the first and second probes are applied as a coating onto an oxygen barrier support layer.

30. The calibration card of claim 29 wherein the oxygen barrier support layer is selected from the group consisting of polyethylene terephthalate, polyvinyl chloride, polyethylene and polypropylene.

31. The calibration card of claim 29 wherein the oxygen barrier support layer is biaxially oriented polyethylene terephthalate.

32. The calibration card of claim 26 wherein the first and second probes are covered by a transparent cover layer.

33. The calibration card of claim 26, wherein the card contains (i) first indicia tagging the first probe to a calibration value of a probe exposed to a near zero concentration of oxygen, and (ii) second indicia tagging the second probe to a calibration value of a probe exposed to an environmental concentration of oxygen.

34. A method of calibrating an analytical instrument having a calibration mode and capable of reading a photoluminescent oxygen probe or plurality of photoluminescent oxygen probes from which the concentration of oxygen in a sample or set of samples communicating with the probe can be determined, comprising the steps of:
(a) obtaining a calibration card according to claim 26,
(b) exposing the second probe to a medium having a known concentration of oxygen,
(c) setting the analytical instrument to calibration mode,
(d) taking a reading from the first probe with the analytical instrument,
(e) correlating the value of the reading to a zero oxygen concentration,
(f) taking a reading from the second probe with the analytical instrument, and
(g) correlating the value of the reading to the known oxygen concentration to which the second probe is exposed.

35. The method of claim 34 wherein the steps of taking a reading from the first and second probes are performed in a predetermined sequence.

36. The method of claim 34 further comprising the step of providing the analytical instrument with data indicating which probe on the calibration card was read first.

37. The method of claim 34 further comprising the step of providing the analytical instrument with data indicating the oxygen concentration of the medium to which the second probe is exposed.

38. The method of claim 34 wherein readings and correlations are based upon photoluminescence lifetime.

* * * * *